United States Patent [19]
Nugent

[11] 4,134,512
[45] Jan. 16, 1979

[54] ONE-WAY EVACUATED TUBE STOPPER

[75] Inventor: Edward L. Nugent, N. Caldwell, N.J.

[73] Assignee: Becton, Dickinson and Company, East Rutherford, N.J.

[21] Appl. No.: 804,502

[22] Filed: Jun. 8, 1977

[51] Int. Cl.² .................. B65D 51/00; A61B 5/14
[52] U.S. Cl. ............................ 215/247; 128/2 F; 128/DIG. 5; 215/260; 422/99
[58] Field of Search .............. 128/2 F, 2 G, 215, 297, 128/350 V, DIG. 5; 215/260, 270, 247; 23/292

[56] References Cited

U.S. PATENT DOCUMENTS

| | | | |
|---|---|---|---|
| 2,969,066 | 1/1961 | Holter et al. | 128/350 V |
| 3,405,706 | 10/1968 | Cinqualbre | 128/DIG. 5 |
| 3,417,750 | 12/1968 | Carson | 128/350 V |
| 3,463,159 | 8/1969 | Heimlich | 128/350 V |
| 3,817,240 | 6/1974 | Ayres | 128/DIG. 5 X |
| 3,848,603 | 11/1974 | Throner | 128/350 V X |
| 3,874,367 | 4/1975 | Ayres | 128/DIG. 5 X |

FOREIGN PATENT DOCUMENTS

| | | | |
|---|---|---|---|
| 242838 | 1/1963 | Australia | 215/260 |
| 1956953 | 6/1970 | Fed. Rep. of Germany | 128/2 F |
| 2233462 | 1/1974 | Fed. Rep. of Germany | 215/260 |
| 2349996 | 2/1974 | Fed. Rep. of Germany | 128/DIG. 5F |

Primary Examiner—Morris O. Wolk
Assistant Examiner—Arnold Turk
Attorney, Agent, or Firm—Kane, Dalsimer, Kane, Sullivan & Kurucz

[57] ABSTRACT

Stopper for an evacuated tube with an open end for collecting fluid such as blood samples. The stopper includes a plug adapted to be mounted in the opening in the tube so as to normally seal the tube. The plug permits access of a fluid sample needle therethrough into fluid communication with the reduced pressure interior of the tube so that fluid is collected in the tube from the needle. A check valve is on the plug to automatically open when the needle is inserted through the plug and subjected to the reduced pressure in the tube and to automatically close when subjected to a predetermined amount of pressure from within the tube such as that caused by backflow thereby preventing any fluid passing into the needle from the tube. The check valve includes a chamber which can be used as a reagent holder prior to the tube use.

16 Claims, 8 Drawing Figures

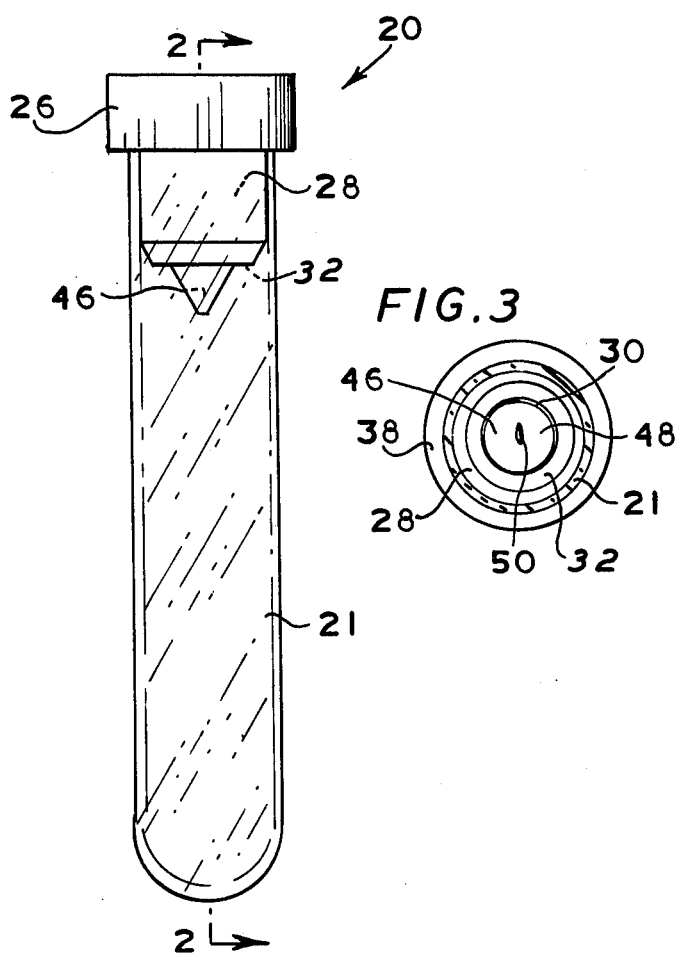
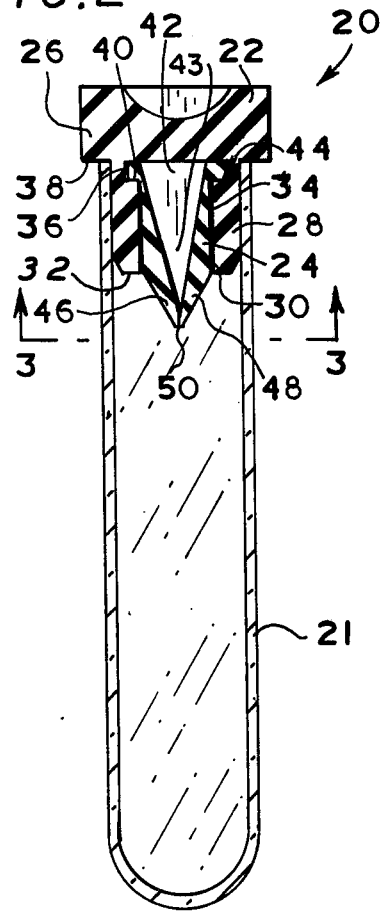
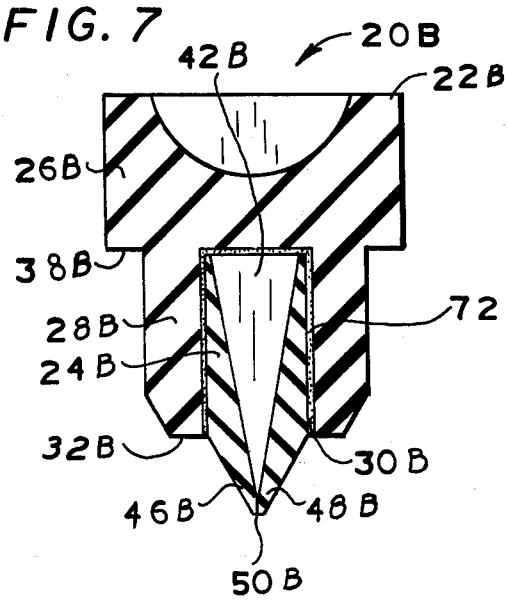
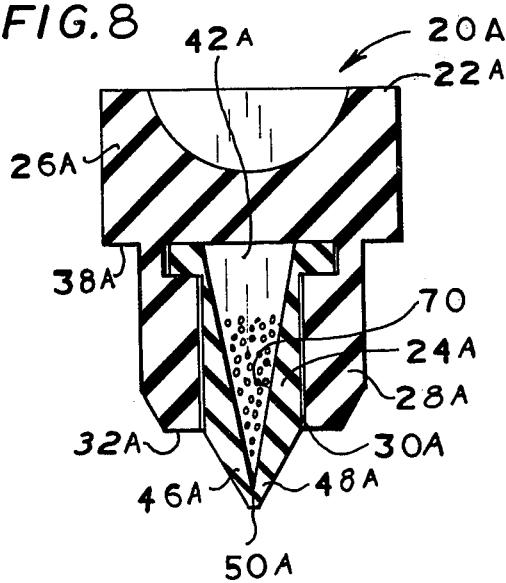

ONE-WAY EVACUATED TUBE STOPPER

BACKGROUND OF THE INVENTION

One method of taking samples of fluid from a patient, such as blood samples, is to utilize a double ended needle in which one end is used to accomplish a veni-puncture and the other end is adapted to be connected to one or more partially or fully evacuated tubes which may or may not contain medicament. The samples are collected due to the pressure differential produced when the interconnection is made. Naturally when collecting samples of fluid such as blood it is desirable to provide a complete fluid path during the collection process but also to avoid any danger of changes in pressure producing backflow of contaminated blood or other fluid, such as medicament, to the patient. Medicaments are contained in the tube for mixtue with the blood and together or independently could flow back through the needle assembly into the patient. Thus, it has been found that various types of check valves can be employed as part of the needle assembly to achieve the necessary protective measures to avoid backflow.

When samples are collected on mass scales, cost is a factor particularly where disposability is desirable and in modern day technology is often of the essence. Therefore, the more complex the needle assembly, the most expensive it becomes and, thus the more undesirable it becomes for disposability purposes. Accordingly, in many instances it is been found to be a more or less prohibitive additional cost to provide complex valving mechanism including a check valve to avoid backflow as part of a disposable low cost needle assembly for collecting single or multiple blood samples.

Therefore, it is of extreme concern that the problem of backflow be avoided while maintaining the needle assembly at the lowest possible cost. Consequently, there is room for improvement in the combination structure utilized for sampling purposes.

SUMMARY OF THE INVENTION

With the above background in mind, it is among the primary objectives of the present invention to provide an improvement to the fluid sampling systems presently in use whereby the cost of manufacture and use is maintained at the lowest possible level and protective means is incorporated in the system to avoid and prevent backflow to the patient of undersirable and contaminating fluids. It is contemplated that a check valve means can be incorporated as part of the sealing stopper for the evacuated or partially evacuated tube thereby avoiding the necessity of including the check valve to prevent backflow as part of the needle assembly and maintaining the minimum possible cost for the needle structure. It has been found that a low cost stopper can be provided with a one-way check valve incorporated thereon which will operate effectively to prevent backflow while not interfering with the collectiion of the sample in the tube when the tube is coupled to the needle assembly connected to the patient. The stopper is designed so that the tube can be utilized with any conventional blood collection needle or similar type of needle utilized today. Furthermore, the tube can be used in and held in any position with the valve operating effectively regardless of position to prevent backflow. Thus, special techniques, such as a downward position of the arm and the tube, are not required. Furthermore, by providing the check valve to prevent backflow as part of the stopper for the evacuated tube, the necessity of sterilization of the interior tube is removed since there is no danger of contaminated backflow leaving the tube.

The valve can also act as a chamber for holding various reagents such as clot activators and anticoagulants. It is provided with an interior chamber to hold the reagent prior to tube use. The reagent is captured within the valve on the stopper which protects the reagent and prevents reagent entrapment between the glass tube and the stopper or in grease barriers on serum separator type collection tubes.

The structure contemplated includes designs whereby the valve is formed as an integral part of the stopper or is formed separately and assembled with the stopper prior to insertion into the tube to form the sealing means for the open end of the tube. Thus, it is possible to form stoppers of new design including the valve as an integral part thereof or providing separate valves to be mounted in existing or modified stoppers presently available and marketed.

In summary, a stopper is provided for an evacuated tube used for collecting fluid samples from a sample collection needle through an opening in one end. The stopper includes a plug adapted to be mounted in the opening in the tube so as to normally seal the tube. The plug has means thereon to permit access of a fluid sample needle therethrough into fluid communication with the reduced pressure interior of the tube so that fluid is collected in the tube from the needle. A check valve on the plug is provided to automatically open when the needle is inserted through the plug and subjected to the reduced pressure in the tube and to automatically close when subjected to a predetermined amount of pressure from within the tube such as that caused by backflow thereby preventing any fluid passing into the needle from the tube.

With the above objectives among others in mind, reference is made to the attached drawings.

BRIEF DESCRIPTION OF THE DRAWINGS

In The Drawings:

FIG. 1 is a side elevation view of the stopper of the invention mounted in an evacuated tube;

FIG. 2 is a sectional elevation view thereof taken along the plane of line 2—2 of FIG. 1;

FIG. 3 is a sectional top view thereof taken along the plane of line 3—3 of FIG. 2;

FIG. 7 is an enlarged sectional view of an alternative embodiment of the stopper of the invention; and FIG. 8 is an enlarged sectional view of a further alternative embodiment of the stopper of the invention.

DESCRIPTION OF THE PREFERRED EMBODIMENT

Figure 4:
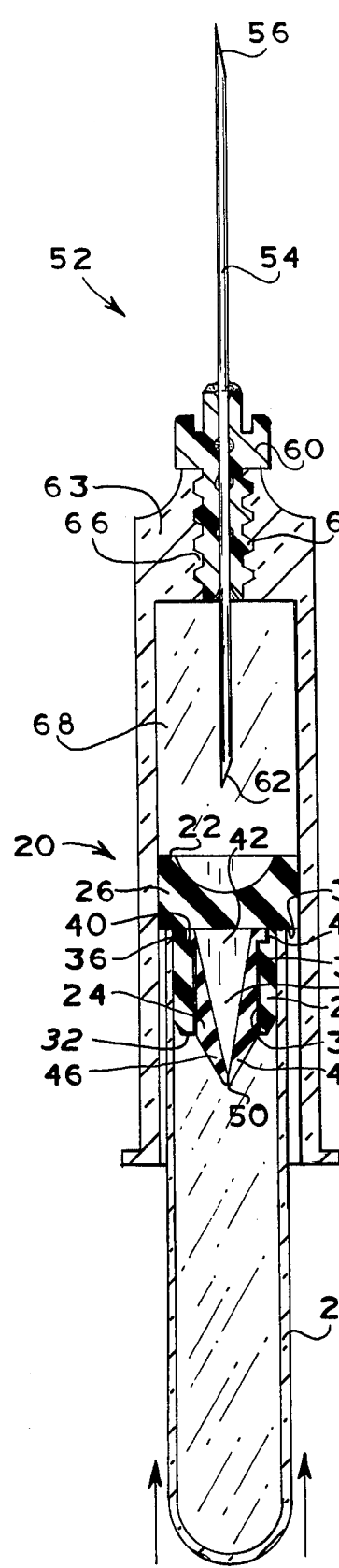
FIG. 4 is a sectional view of the stopper mounted in an evacuated tube in position in a holder for coupling with a blood sampling needle.

Stopper 20 as shown in FIGS. 1–6 includes a two part assembly, a plug 22 and a check valve 24. Plug 22 is formed of conventional stopper material used for closing evacuated tubes such as natural or synthetic rubber or a resilient plastic as long as the matrial is puncturable and self-sealing. The plug includes an enlarged head 26 and a reduced diameter cylindrical body 28 extending from the head. The head and body are shown as a one-piece construction with the head being of larger diameter and also shown as a cylindrical disc.

A recess 30 extends inwardly from end 32 distal from head 26. The recess 30 is formed of a first portion 34 of smaller diameter extending inwardly from end 32 and communicating with a larger diameter portion 36 adjacent to the undersurface 38 of head 26. The communicating surfaces forming larger diameter portion 36 and smaller diameter portion 34 form an annular shoulder 40 on the interior surface of body 28.

Positioned in recess 30 is a check valve 24. The check valve has one open end 42 surrounded by a flange 44 which is large enough to seat on shoulder 40 in recess 30. Extending rearwardly from open end 42 is a pair of spaced flaps 46 and 48 which normally tend to extend toward one another so as to form a sealed end 50 distal from open end 42 in the normal relaxed position. Introduction of pressure from end 42 through the hollow interior of check valve 24 will force flaps 46 and 48 apart thereby providing a through passageway. Conversely, pressure from the other end of check valve 24 will tend to push flaps 46 and 48 toward one another to more tightly seal end 50 and prevent fluid from flowing through the check valve to open end 42.

Check valve 24 can be coupled with plug 26 in conventional fashion such as by extending the check valve into the recess 30 unitl it snaps into position with flange 44 seated between shoulder 40 and the undersurface 38 of head 26. Check valve 24 is also formed of a conventional self-sealing elastomeric material such as natural or synthetic rubber or plastic of similar properties so that it can be easily assembled with and be compatable with plug 22.

The stopper 20 is easily assembled with tube 21 by pressing body portion 28 into the tube, the body portion having a slightly larger outer diameter than the inner diameter of the tube opening so that there is frictional and sealing interengagement between the outer wall of body 28 and the inner wall of tube 21. The stopper is inserted until the undersurface 38 of head 26 seats on the rim of the open end of tube 21. The assembled stopper and tube are then ready for use. The tube contains a conventional partial or complete vacuum and may additionally contain medicaments such as anticoagulants for blood collection purpose. Tube 21 is formed of an inexpensive glass or plastic material.

The stoppered tube is then ready for assembly to a conventional device for introduction of fluid to the tube from a source such as the vein of a patient. It is common to utilize a conventional double ended needle for collecting blood samples in one or more evacuated tubes. Therefore, for example purposes, the stopper and inteconnected tube of the present invention is depicted in cooperation with a needle assembly of this type. Naturally it is readily usable with other types of fluid sampling systems with a needle being employed to introduce the fluid to the evacuated tube.

In the depicted embodiment a double ended needle assembly 52 is shown with a double ended needle 54 having a tip 56 for introduction to a vein 57 of a patient for collecting blood. Needle 54 is mounted in a hub 60 intermediate the ends of the needle by conventional means such as epoxy. The rear tip 62 of needle 54 extends behind hub 60 in position for introduction into tube 21 through stopper 20.

Hub 60 with interconnected needle 54 is mounted in a conventional holder 63 by threaded interengagement between threads 64 on the rear portion of the hub and a corresponding threaded passageway 66 through the holder. Coupled with the holder venipuncture tip 56 extends forwardly of the holder and the opposite pointed end 62 of the needle extends into interior chamber 68 in the holder in position for coupling with the stoppered tube 21.

Figure 5:
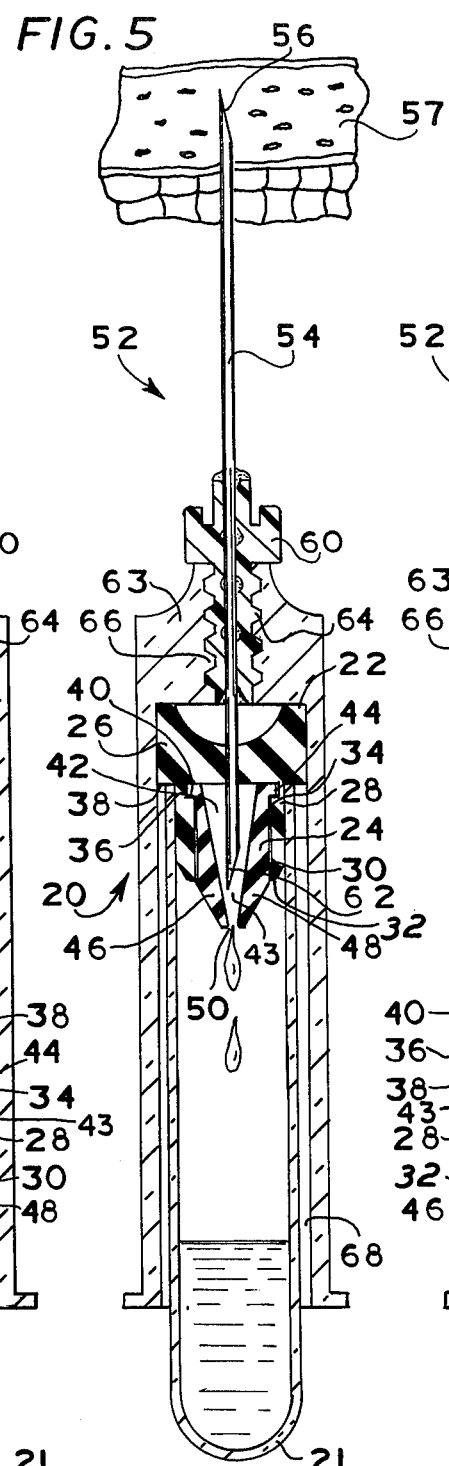
FIG. 5 is a sectional view thereof showing the stopper in the tube in coupled relationship with a blood sampling needle located in the vein of a patient so that blood is being collected within the tube.

The coupled holder and needle assembly in position for interengagement with stopper tube 21 prior to insertion into the vein for collection of the sample is depicted in FIG. 4. In FIG. 5, tip 56 has been inserted into the vein 57 to permit blood to flow through the needle and the rear tip 62 of the needle has been inserted through plug 22 of the stopper into opening 42 in check valve 24. In this position, the difference in pressure between the interior of the evacuated tube 21 and the blood flowing from the vein through needle 54 causes flaps 46 and 48 to open so that blood is free to flow and collect within tube 21.

Figure 6:
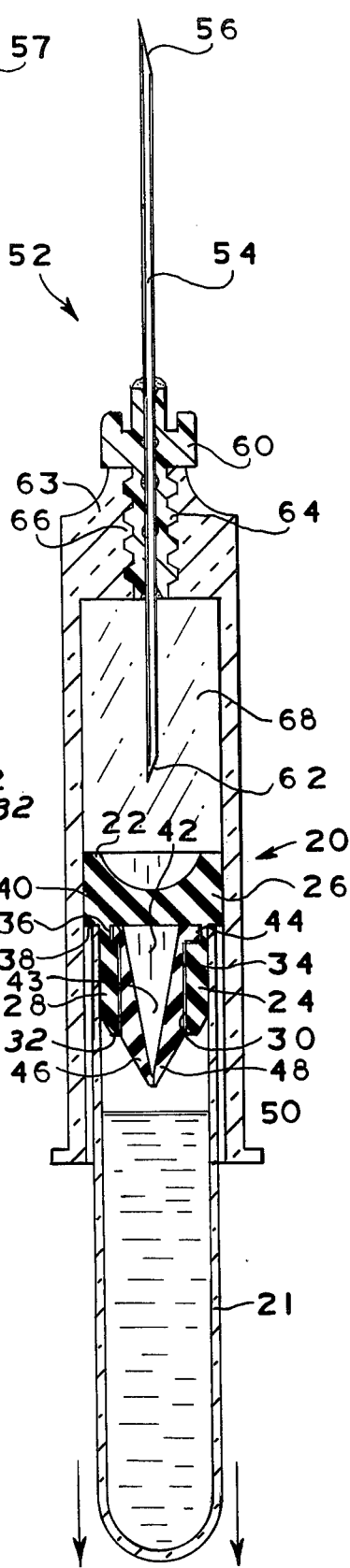
FIG. 6 is a sectional view thereof showing the stopper mounted in the tube containing a blood sample having been removed from interconnection with a blood sampling needle.

When the pressures are equalized and the sample has been fully collected the pressure differential will be relaxed and flaps 46 and 48 will return to the relaxed position sealing the end of the check valve. The tube and interconnected stopper can then be removed from the needle 54 whereupon the self-sealing stopper will once again close the open end of the tube as depicted in FIG. 6. Should any pressure build-up occur within tube 21 as the sample is being collected in tube 21 and the balance of pressure disturbed, the increase in pressure within the tube will cause flaps 46 and 48 to immediately close thereby preventing a backflow through the needle assembly into the patient. By avoiding backflow, contaminating bacteria within the tube is not permitted to leave the tube nor is any medicament or other fluid contained within the tube allowed to pass back through the needle assembly to the patient. Thus, the stopper 20 including the oneway check valve 24 permits flow of blood or similar fluid in one direction into tube 21 and prevents backflow into needle 54 or the patient. Accordingly, there is no contamination of needle assembly 52 or the patient while a sample is being collected.

The arrangement of stopper 20 including check valve 24 is designed so that the tube can be used with any conventional needle as discussed above. Furthermore, the tube can be used in any position so as to eliminate special technique for downward position of the arm of a patient or of the tube. Sterilization of the tube is not required since there is no danger of contaminated backflow.

Also, in addition to the embodiment depicted as a two-piece assembly of a plug and check valve, it is possible to form the two elements as a single integral unit such as a molded one-piece plug and check valve which can be inserted in the same fashion as described above within a tube identical to tube 21 and which will operate in the same manner. A stopper of either the two-piece or one-piece type is inexpensive to manufcture particularly in mass amounts and accordingly lends itself to disposability. Additionally, there is no necessity of additional cost being incurred when manufacturing needle assemblies such as assembly 52 thus retaining their disposability and low cost.

Flaps 46 and 48 of the check valve are in engagement at one end of the valve and the upper portion of the valve adjacent to opening 42 is open to form a chamber 43. As depicted in the drawings chamber 43 normally receives the end 62 of needle 54 during use of the assembly. However, prior to use chamber 43 which is sealed by the closed flaps 46 and 48 at one end and at the other end by the under surface of head 26 of the stopper in engagement with flange 44 of the valve forms a sealed compartment or holder for a typical reagent. The reagent 70, as depicted in stopper 20a of FIG. 8, can be any of a variety of different clot activators or anticoagulants. The reagent 70 can be held in chamber 43 until the tube is used. With the reagents being protected in the closed chamber 43, reagent entrapment between the glass tube and the stopper or in grease barriers on serum separator type collection tubes is prevented. For example, a reagent such as a silica powder can be stored in chamber 43 and will serve as a blood clotting activator. Naturally if only the feature of protection against backflow is desired, then the valve chamber 43 can be left without any reagents therein as discussed above. However, with reagent in chamber 43, when the blood flows through needle 54 and out through opening 62 in the needle, it rinses the reagent in chamber 43 into the interior of tube 21 to mix with and in some cases dissolve with the blood sample. This is naturally dependent upon the reagent system used. Thus, instantaneous mixing of the reagent with the blood sample is provided as soon as the blood draw is initiated. With the exception of reagent 70, stopper 20a is identical with stopper 20 of FIGS. 1–6 and is used in the same manner.

FIG. 7 shows a further embodiment in stopper 20b. Check valve 24b has substantially the same outer diameter throughout its length. Similarly, recess 30b in plug 22b has a corresponding recess of substantially the same diameter throughout its length. The valve 24b is held in position by an appropriate adhesives 72. Stopper 20b operates in the same manner as the two previously discussed embodiments. The difference in structure resides in the elimination of the flange and shoulder arrangements between the check valve and plug. Adhesives holds the valve in positiion. Naturally it would also be possible to use adhesives to hold the parts of stoppers 20 and 20a together along with the flange and shoulder interengagement.

Thus the several aforenoted objects and advantages are most effectively attained. Although several somewhat preferred embodiments have been disclosed and described in detail herein, it should be understood that this invention is in no sense limited thereby and its scope is to be determined by that of the appended claims.

I claim:

1. A stopper adapted for removable mounting in an evacuated tube having an open end for collecting blood samples, the stopper comprising; a plug adapted to be mounted in the open end of an evacuated tube so as to normally seal the open end of the tube, the plug having means thereon puncturable by a sample needle to permit access of a blood sample needle therethrough into fluid communication with the evacuated interior of the tube so that blood is collected in the tube from the needle, a normally closed check valve on the plug capable of automatically opening when the needle is inserted through the plug and is subjected to the reduced pressure in the tube and automatically closing when subjected to a predetermined amount of pressure from within the tube such as that caused by backflow thereby preventing any fluid passing into the needle from the tube, the check valve having surfaces thereon cooperating with surfaces on the plug to form a sealed interior chamber therebetween when the valve is closed, and the chamber being positioned to be capable of housing the end of the needle when the needle is inserted through the plug to thereby facilitate operation of the valve in controlling flow into and out of the needle.

2. The invention in accordance with claim 1 wherein the plug is constructed of a material that automatically reseals the tube after the needle has been removed therefrom.

3. The invention in accordance with claim 1 wherein the plug is formed of a self-sealing, elastomeric, puncturable material.

4. The invention in accordance with claim 1 wherein the plug contains means to be frictionally mounted in the open end of the tube.

5. The invention in accordance with claim 1 wherein the plug is formed of natural rubber.

6. The invention in accordance with claim 1 wherein said sealed interior chamber is adapted to contain reagent material positioned so that upon introduction of blood from the needle and opening of the check valve, the blood will mix with the reagent and be introduced simultaneously into the tube therewith.

7. The invention in accordance with claim 1 wherein the check valve is a valve member formed of self-sealing elastomeric material and including two adjacent resilient flaps normally resting against one another in the closed position at one end on the check valve, the check valve having a passageway therethrough and being open at the other end whereby pressure from the open end will separate the flaps opening the valve and forming a passageway therethrough, and removal of the pressure or a greater pressure from the one end of the valve will permit the two flaps to come together into the normal closed position so that fluid is free to flow in one direction through the valve but is not permitted to flow in the other direction through the valve.

8. The invention in accordance with claim 7 wherein the plug has an enlarged head portion and a tubularly-shaped hollow body portiion extending from the head portion, the adjoining surfaces of the body portion and the head portion forming a shoulder adapted to be seated against the rim on the open end of a tube with the body portion inserted in the tube and in frictional engagement with the side walls of the tube, the body portion of the plug containing a central recess extending inwardly from the end opposite to the head and terminating in an annular receiving recess of larger diameter, the check valve being mounted in the recess with a rim portion at the open end of the valve seated in the larger recess adjacent the head of the plug and the flaps extending toward the end of the plug distal from the head beyond the open end of the plug so that the valve is captured within the body portion of the plug and positioning the valve so that when the plug is placed in interengagement with the tube the valve will extend beyond the end of the body of the plug into the tube.

9. A fluid sample collection container comprising; an evacuated tube having an open end, a stopper mounted in the open end of the tube, the stopper including a plug mounted in the opening in the tube so as to normally seal the tube, the plug having means thereon puncturable by a sample needle to permit access of a fluid sample needle therethrough into fluid communication with the reduced pressure interior of the tube so that fluid is collected in the tube from the needle, a normally closed check valve on the plug capable of automatically opening when the needle is inserted through the plug and subjected to the reduced pressure in the tube and automatically closing when subjected to a predetermined amount of pressure from within the tube such as that caused by backflow thereby preventing any fluid passing into the needle from the tube, the check valve having surfaces thereon cooperating with surfaces on the plug to form a sealed interior chamber therebetween when the valve is closed, and the chamber being positioned to be capable of housing the end of the needle when the needle is inserted through the plug to thereby facilitate operation of the valve in controlling flow into and out of the needle.

10. The invention in accordance with claim 9 wherein the plug is constructed of a material that automatically reseals the tube when the needle is removed therefrom.

11. The invention in accordance with claim 9 wherein the plug is in the form of self-sealing, elastomeric, puncturable material.

12. The invention in accordance with claim 9 wherein the plug contains means for frictionally mounting the plug on the open end of the tube.

13. The invention in accordance with claim 9 wherein the plug is formed of natural rubber.

14. The invention in accordance with claim 9 wherein said sealed interior chamber is adapted to contain reagent material positioned so that upon introduction of blood from the needle and opening of the check valve, the blood will mix with the reagent and be introduced simultaneously into the tube therewith.

15. The invention in accordance with claim 9 wherein the check valve is a valve member formed of self-sealing elastomeric material and including two adjacent resilient flaps normally resting against one another in the closed position at one end on the check valve, the check valve having a passageway therethrough and being open at the other end whereby pressure from the open end will separate the flaps opening the valve and forming a passageway therethrough, and removal of the pressure or a greater pressure from the one end of the valve will permit the two flaps to come together into the normally closed position so that fluid is free to flow in one direction through the valve but is not permitted to flow in the other direction through the valve.

16. The invention in accordance with claim 15 wherein the plug has an enlarged head portion and a tubularly-shaped hollow body portion extending from the head portion, the adjoining surfaces of the body portion and the head portion forming a shoulder seated against the rim on the open end of a tube with the body portion inserted in the tube and in frictional engagement with the side walls of the tube, the body portion of the plug containing a central recess extending inwardly from the end opposite to the head and terminating in an annular receiving recess of larger diameter, the check valve being mounted in the recess with a rim portion at the open end of the valve seated in the larger recess adjacent the head of the plug and the flaps extending toward the end of the plug distal from the head beyond the open end of the plug thereby capturing the valve within the body portion of the plug and positioning the valve so that when the plug is placed in interengagement with the tube the valve will extend beyond the end of the body of the plug into the tube.

* * * * *